(12) United States Patent
Pa et al.

(10) Patent No.: US 8,713,989 B2
(45) Date of Patent: May 6, 2014

(54) RESTRICTED LINE OF SIGHT DESIGN FOR INLET LINER

(75) Inventors: Ponna Peter Pa, Bear, DE (US); William H Wilson, Newark, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 518 days.

(21) Appl. No.: 13/070,070

(22) Filed: Mar. 23, 2011

(65) Prior Publication Data
US 2012/0240661 A1 Sep. 27, 2012

(51) Int. Cl.
*G01N 30/60* (2006.01)
*B01D 53/02* (2006.01)

(52) U.S. Cl.
USPC .............. 73/23.39; 73/23.41; 96/105

(58) Field of Classification Search
USPC ........... 73/23.39, 23.41, 23.42; 96/105; 422/502; 436/174
See application file for complete search history.

(56) References Cited

U.S. PATENT DOCUMENTS

| | | | |
|---|---|---|---|
| 4,035,168 | A | 7/1977 | Jennings |
| 4,124,358 | A | 11/1978 | Muller |
| 5,119,669 | A | 6/1992 | Silvis et al. |
| 5,760,291 | A | 6/1998 | Abdel-Rahman |
| 6,062,065 | A | 5/2000 | Sugimoto et al. |
| 6,093,371 | A | 7/2000 | Wilson |
| 6,134,945 | A | 10/2000 | Gerstel et al. |
| 6,494,939 | B1 | 12/2002 | Tipler |
| 6,498,042 | B1 | 12/2002 | Wilson |
| 6,929,780 | B2 | 8/2005 | Gerstel |
| 6,955,709 | B2 | 10/2005 | Magni |
| 7,311,757 | B2 | 12/2007 | Tipler et al. |
| 7,572,319 | B2 | 8/2009 | Tipler et al. |
| 8,366,814 | B2 * | 2/2013 | Jones et al. .............. 96/105 |
| 2009/0183634 | A1 | 7/2009 | Zeeuw et al. |

OTHER PUBLICATIONS

SGE Analytical Science, Products—Varian Liners. Published online on Aug. 30, 2007. Accessed online on Aug. 27, 2013 at <http://web.archive.org/web/20070830224917/http://www.sge.com/products/product-selection/select-by-instrument/varian/>.*
Stidsen, G. B., Goss, M. A., Rightnour, B. R., and Barone, G. A., "Review of Liner Selection Criteria for Gas Chromatographic Analysis," pp. 1-28. Published online in 2002. Accessed online Aug. 27, 2013 at <www.restek.com/pdfs/pres-2002-278.pdf>.*
Grob, K., et al., Video-taped sample evaporation in hot chambers simulating gas chromatography split and splitless injectors II. Injection with band formation, J. Chromatogr. A 897 (2000) 247-258.

(Continued)

*Primary Examiner* — Lisa Caputo
*Assistant Examiner* — Punam Roy
(74) *Attorney, Agent, or Firm* — Milstein Zhang & Wu LLC

(57) ABSTRACT

An inlet liner is provided for use in an inlet assembly of a chromatograph system. The inlet liner has an elongate tube that extends along a longitudinal axis and defines a bore that extends along the longitudinal axis and has an inner bore surface. At least one projection extends from the inner bore surface into the bore. Chromatograph systems are provided including the exemplary inlet liner(s). Methods are also provided for analyzing a sample containing a matrix in a chromatograph system having an inlet assembly connected to a chromatograph column. The method includes positioning an exemplary inlet liner in the inlet assembly, flowing the sample through the inlet liner, and adhering a portion of the matrix to a projection surface of at least one projection of the inlet liner.

19 Claims, 7 Drawing Sheets

(56) References Cited

OTHER PUBLICATIONS

Fedorak, P.M., et al., Decomposition of two methylbenzothiophene sulphoxides in a commercial gas chromatography injection port liner, J. Chromatogr. 591(1992) 362-366.

Saito, K., et al., Application of a Novel Large-Volume Injection Method Using a Stomach-Shaped Inlet Liner in Capillary Gas Chromatographic Trace Analysis of Dioxins in Human Milk and Plasma, Anal. Sci. 23, 661-666 (2007).

Corso, T.N., et al., Gas Chromatograph Injection Liner for Continuous Analyte Admission into a Mass Spectrometer, Anal. Chem. 70(5), 1030-1032 (1998).

Staniewski, J., et al., Solvent elimination rate in temperature-programmed injections of large sample volumes in capillary gas chromatography, J. Chromatogr. 623 (1992) 105-113.

Kagel, J.R., et al., Improving ion-trap GC-MS quantitation limits for therapeutic agents extracted from rat plasma, J. Pharm. Biomed. Anal. 16 (1998), 1261-1265.

Grob, K., Injection Techniques in Capillary GC, Anal. Chem. 66(20), 1009A-1019A (Oct. 15, 1994).

Lee, M.L., et al., Open Tubular Column Gas Chromatography, Theory and Practice, John Wiley and Sons, New York, 1984, pp. 111-126.

\* cited by examiner

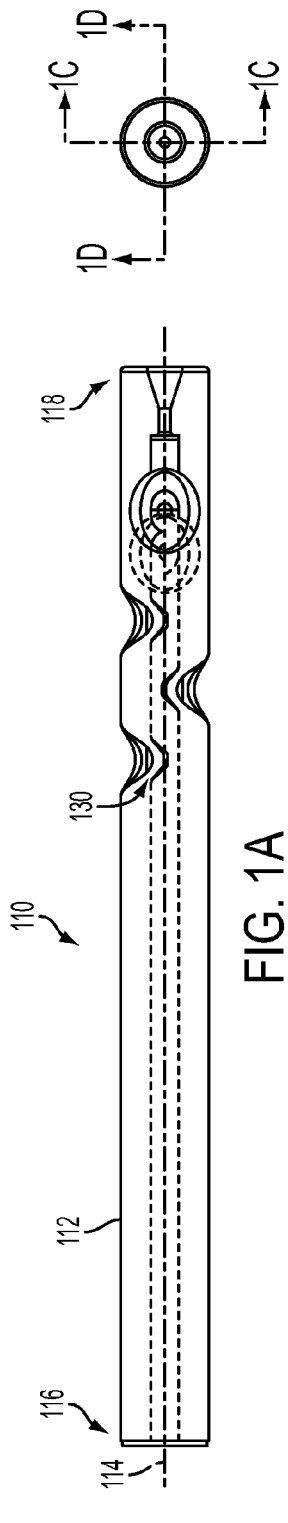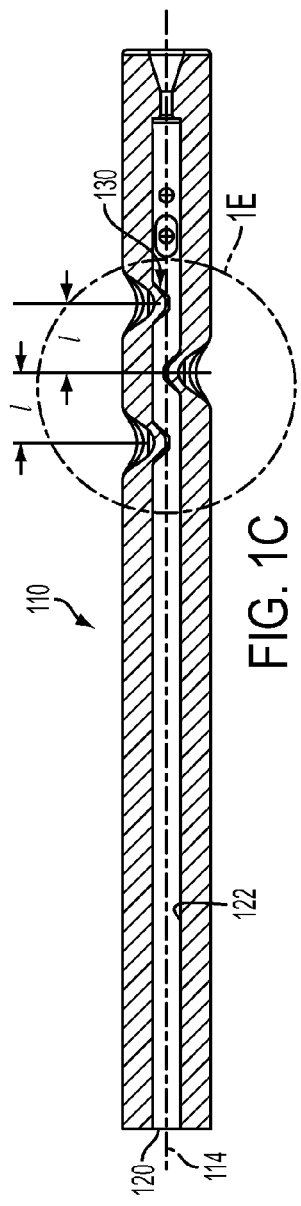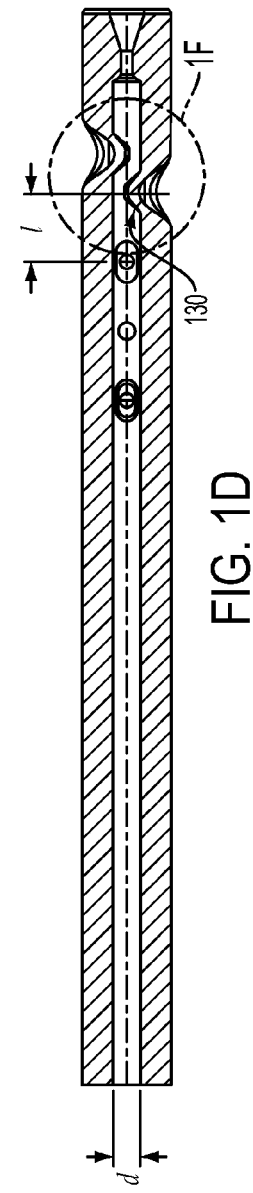

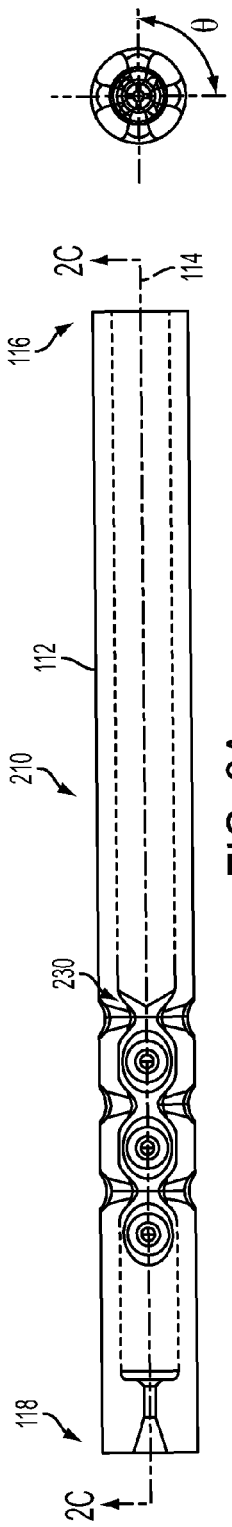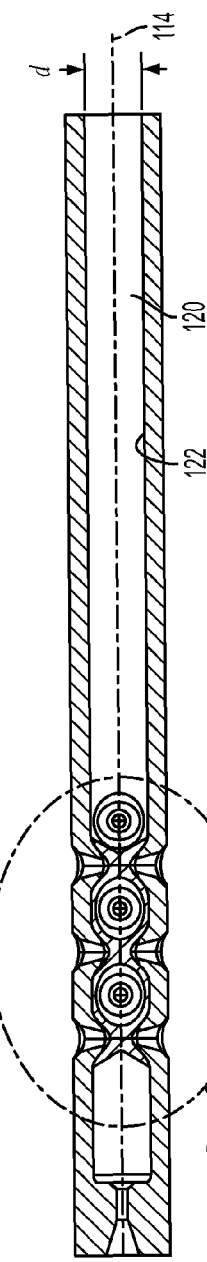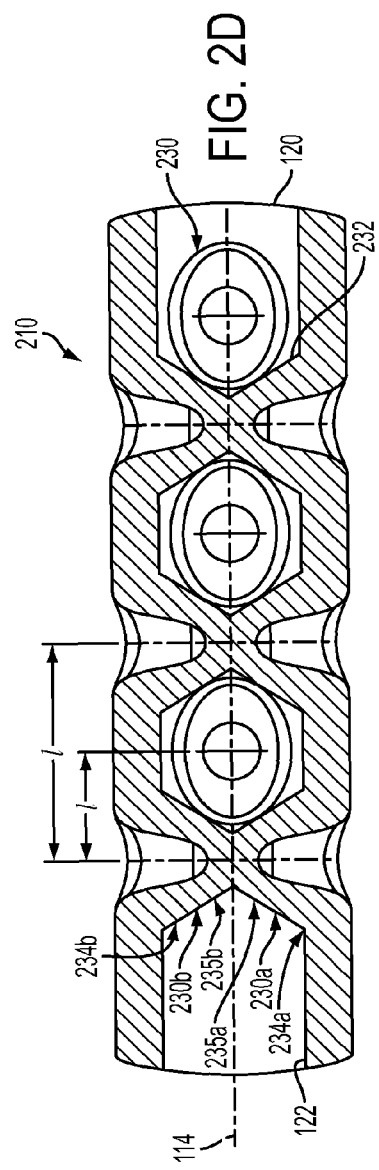

RESTRICTED LINE OF SIGHT DESIGN FOR INLET LINER

FIELD OF THE INVENTION

This invention relates generally to the field of inlet liners for use in an inlet assembly of a chromatograph system.

BACKGROUND OF THE INVENTION

In gas chromatography, a sample is introduced to the column of the chromatograph system via an inlet. To reduce the adsorption or decomposition of analytes in the sample, an inlet liner is typically installed inside the inlet. The inlet liner must contain the sample prior to passing the sample to the column, in order to isolate the sample from any active sites inside the inlet that could decompose the analytes in the sample. Inlet liners should also contain or trap involatile materials in the sample to minimize or prevent them from entering the column; the more involatile materials that enter the column, the more frequently the chromatograph system will need to be cleaned, which results in significant operational inefficiencies.

In order to contain the sample, inlet liners have been designed that contain a plug of glass wool that is used to trap involatile materials. While the glass wool plug does trap involatile materials, it is also difficult to chemically deactivate. As a result, compounds will irreversibly adsorb to the glass wool or chemically decompose on its surface. Thus, some inlet liners that are used contain no glass wool; while these liners do not suffer from the drawbacks of those containing a glass wool plug, they are equally deficient because they allow the sample to leave the liner and interact with active sites in the inlet. Inlet liners have also been designed that have a helical path for the sample to travel through. These inlet liners also have drawbacks because any involatile material in the sample will get trapped at the inlet of the helix and act as an adsorptive trap for the remaining analytes in the sample. Thus, these liners typically need to be replaced frequently in order for the chromatograph system to operate cleanly and efficiently.

Thus, there is a need in the art for inlet liners that can contain or trap involatile materials in a sample without blocking the flow of the sample through the inlet liner and thereby decomposing analytes in the sample. There is also a need in the art for inlet liners that can be used for repeated analyses without the need to be frequently cleaned or replaced.

BRIEF DESCRIPTION OF THE DRAWINGS

The accompanying drawings, which are incorporated in and constitute a part of this specification, illustrate several aspects of the invention and together with the description, serve to explain the principles of the invention.

FIG. 1A is a side elevational view of an exemplary inlet liner, according to one aspect.

FIG. 1B is an end view of the output end of the inlet liner of FIG. 1A.

FIG. 1C is a cross-sectional view of the inlet liner of FIG. 1A taken along line 1C-1C of FIG. 1B.

FIG. 1D is a cross-sectional view of the inlet liner of FIG. 1A taken along line 1D-1D of FIG. 1B.

FIG. 2A is a side elevational view of an inlet liner, according to another aspect.

FIG. 2B is an end view of the input end of the inlet liner of FIG. 2A.

FIG. 2C is a cross-sectional view of the inlet liner of FIG. 2A taken along line 2C-C of FIG. 2A.

FIG. 2D is a cross-sectional view of the inlet liner of FIG. 2A on an enlarged scale as shown in circle 2D of FIG. 2C.

DETAILED DESCRIPTION

Figure 1E:
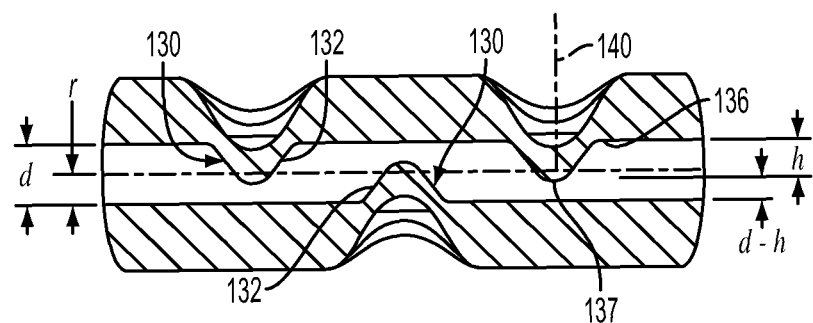
FIG. 1E is a cross-sectional view of the inlet liner of FIG. 1A on an enlarged scale as shown in circle 1E of FIG. 1C.

According to various embodiments, an inlet liner is provided for use in an inlet assembly of a chromatography system. The inlet liner can comprise an elongate tube that extends along a longitudinal axis and has an input end and an oppositely disposed output end. The tube can define a bore that extends along the longitudinal axis and has an inner bore surface. The inlet liner can also comprise at least one projection that extends from the inner bore surface into the bore.

In various other embodiments, a chromatograph system is provided that comprises a chromatography column, an analyzer in fluid communication with the chromatograph column, an inlet assembly connectable to the chromatograph column, and an inlet liner positionable in the inlet assembly. The inlet liner can comprise an elongate tube that extends along a longitudinal axis and has an input end and an oppositely disposed output end that is in fluid communication with the chromatograph column. The tube can define a bore that extends along the longitudinal axis and has an inner bore surface, the tube being configured to pass the sample to the chromatograph column. The inlet liner can also comprise at least one projection that extends from the inner bore surface into the bore.

According to yet other embodiments, a method is provided for analyzing a sample containing a matrix in a chromatograph system having an inlet assembly connected to a chromatograph column. The method can comprise positioning an inlet liner in the inlet assembly. The inlet liner can comprise an elongate tube that extends along a longitudinal axis and has an input end and an oppositely disposed output end. The tube can define a bore that extends along the longitudinal axis and has an inner bore surface. The inlet liner can also comprise at least one projection that extends from the inner bore surface into the bore, the projection(s) having a respective projection surface that is oriented transverse to the longitudinal axis. The inlet liner can be positioned in the inlet assembly such that the output end is in fluid communication with the chromatograph column. The exemplary method can also comprise injecting the sample into the input end of the inlet liner and vaporizing at least a portion of the sample. The method can also comprise flowing the sample through the inlet liner toward the chromatograph column and adhering a portion of the matrix to the projection surface of the at least one projection.

The present invention may be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to a "projection" can include two or more such projections unless the context indicates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Reference will now be made in detail to the present preferred aspects of the invention, examples of which are illustrated in the accompanying drawings. Wherever possible, the same reference numbers are used throughout the drawings to refer to the same or like parts.

As shown in FIGS. 1A-1F, disclosed herein is an exemplary inlet liner 110 for use in an inlet assembly of a chromatograph system. Another exemplary inlet liner 210 is shown in FIGS. 2A-2D. As shown in FIGS. 1A and 2A, an exemplary inlet liner (110 or 210) can comprise a tube 112 that extends along a longitudinal axis 114. The elongate tube 112 can have an input end 116 and an oppositely disposed output end 118. The elongate tube can define a bore 120 that extends along the longitudinal axis 114 and has an inner bore surface 122. The bore can have a substantially circular cross section, an elliptical cross section, or other shaped cross section. The bore can have an inner diameter d proximate to the input end 116 of about 1 mm to about 6 mm. In a particular example, the bore can have an inner diameter of about 2 mm. However, it is contemplated that a bore having any inner diameter can be used, and the exemplary dimensions described herein are not intended to be limiting.

As shown in FIGS. 1C and 1E, the inlet liner 110 can comprise at least one projection 130 that extends from the inner bore surface 122 into the bore 120. Similarly, the inlet liner 210, as shown in FIG. 2D, can comprise at least one projection 230 that extends from the inner bore surface 122 into the bore 120. In one example, the inlet liner can comprise a plurality of projections. The plurality of projections can comprise 2 to 12 projections. Optionally, the plurality of projections can comprise 3 to 7 projections. According to one example, the plurality of projections comprises 5 projections, such as shown in FIG. 1A. In another example, the plurality of projections comprises 12 projections, such as shown in FIG. 2A. The number of projections shown in these figures is exemplary and is not intended to be limiting.

The plurality of projections can comprise at least a first projection and a second projection. The first and second projections can be in spaced relation relative to one another longitudinally on the inner bore surface. For example, the projections can be spaced from each other at a distance, l, as shown in FIGS. 1C-1D, 1F and 2D. As used in these figures, the reference character l is intended to depict a general distance, with no specific value; in other words, as shown in FIG. 2D, two distances between projections are labeled as l, where these values are not necessarily equal. In one aspect, the plurality of projections can comprise more than two projections, and each projection can be spaced from a neighboring projection at a predetermined distance l, such that each projection is substantially equally spaced from each neighboring projection. It is contemplated, however, that the projections can be spaced at unequal distances. In one example, at least two projections can be spaced at a distance ranging from about 1 mm to about 10 mm. In another example, at least two projections can be spaced at a distance ranging from about 3 mm to about 6 mm.

In another aspect, the first and second projections can be in spaced relation relative to one another angularly about the longitudinal axis. As shown in FIG. 2B, for example, the projections can be spaced at an angle, $\theta$, relative to one another about the longitudinal axis. The angle $\theta$ can be from about 10 degrees to about 180 degrees. Optionally, the angle $\theta$ can be from about 30 degrees to about 120 degrees, or from about 45 degrees to about 90 degrees. In one particular example, the angle $\theta$ can be about 90 degrees. For example, with reference to the exemplary inlet liner 110 shown in FIG. 1A, the plurality of projections can comprise 5 projections 130, and at least one pair of the 5 projections can be spaced at an angle of about 90 degrees from each other. Furthermore, at least 4 of the 5 projections can be spaced at an angle of about 90 degrees from each other projection, such that at least one projection is positioned at each of a 0 degree, 90 degree, 180 degree, and 270 degree position about the longitudinal axis. Similarly, as shown in FIG. 2A, the plurality of projections can comprise 12 projections 230, with at least 4 of the 12 projections positioned at each of a 0 degree, 90 degree, 180 degree, and 270 degree position about the longitudinal axis.

Figure 3A:
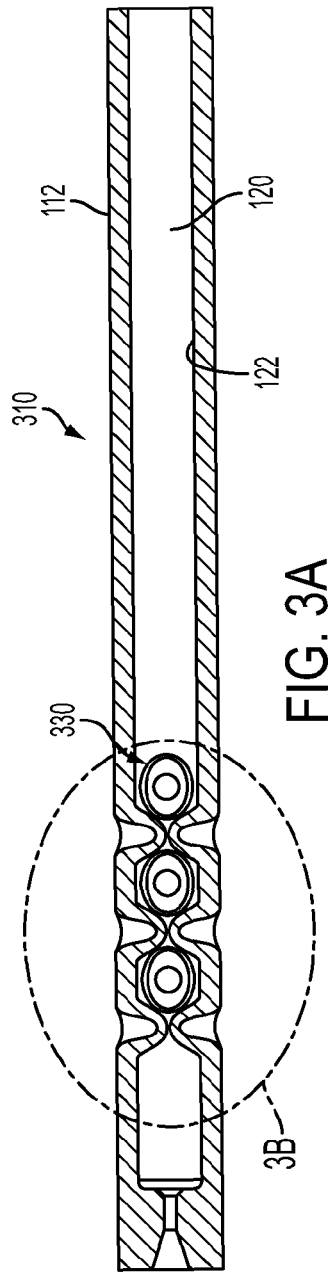
FIG. 3A is a cross-sectional view of an exemplary inlet liner, according to one aspect.
Figure 3B:
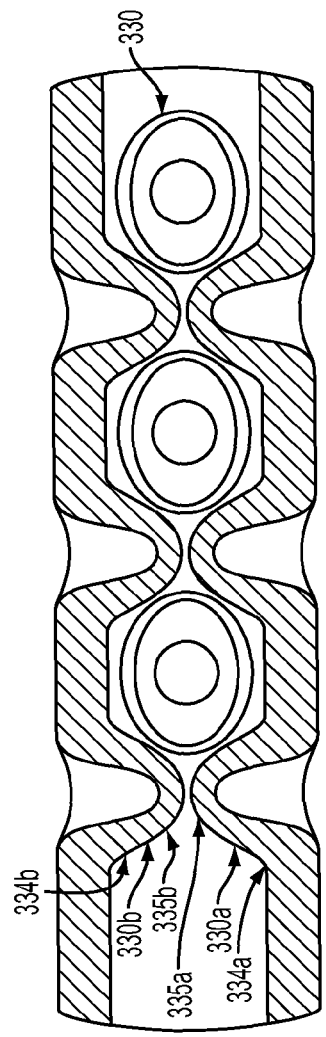
FIG. 3B is a cross-sectional view of the inlet liner of FIG. 3A on an enlarged scale as shown in circle 3B of FIG. 3A.

In one aspect, such as shown in FIG. 2D, each projection (such as projection 230a) can comprise a proximal portion 234a attached to the inner bore surface 122 and a distal portion 235a extending into the bore. In one example, the distal portion of a first projection can be positioned adjacent the distal portion of a second projection. In this example, the distal portions of the first and second projections can be positioned near, but not necessarily abutting each other. For example, as shown in FIG. 3B, the distal portion 335a of a first projection 330a is positioned near—but does not abut— the distal portion 335b of a second projection 330b.

Figure 4A:
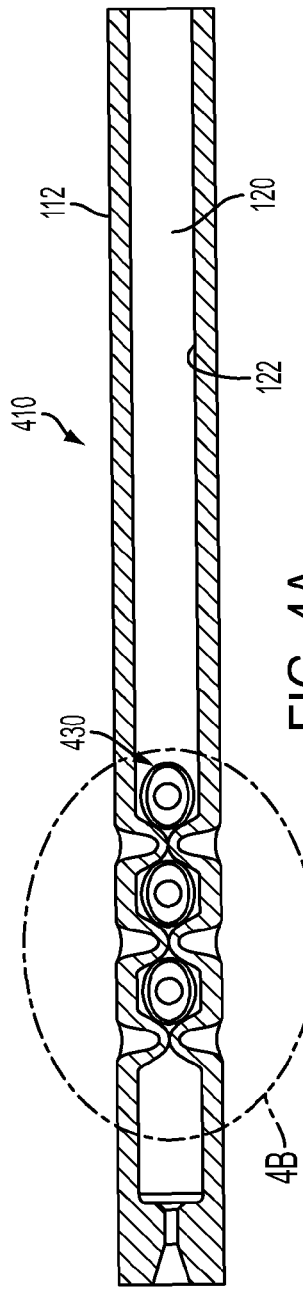
FIG. 4A is a cross-sectional view of an exemplary inlet liner, according to one aspect.
Figure 4B:
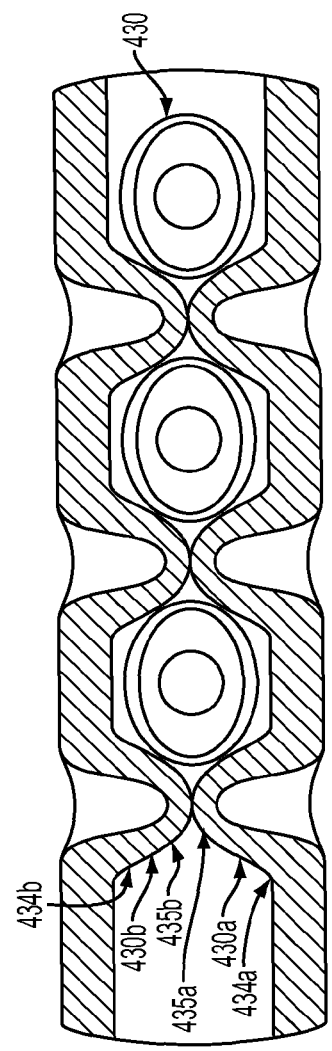
FIG. 4B is a cross-sectional view of the inlet liner of FIG. 4A on an enlarged scale as shown in circle 4B of FIG. 4A.

Optionally, the distal portions of the first and second projections can be in abutting relationship to one another. For example, as shown in FIG. 2D, the first projection 230a and second projection 230b can be in spaced relation relative to one another at an angle of about 180 degrees measured about the longitudinal axis 114, with the distal portion 235a of the first projection and the distal portion 235b of the second projection being in abutting relationship to each other. In this example, the plurality of projections can comprise 12 projections, formed as 6 pairs of projections. The distal portions of each projection in the pairs of projections can be in abutting relationship to each other. Furthermore, in this example, the projections 230 can be formed such that the two opposing projections in each pair are unitary or contiguous with respect to each other. In other aspects, such as shown in FIG. 4B, the projections can be in substantially abutting relationship, but are not formed to be unitary or contiguous with respect to opposing projections. For example, the distal portion 435a of a first projection 430a can be in substantially abutting relationship with the distal portion 435b of a second projection 430b.

In some exemplary aspects, the inlet liner can comprise a plurality of projections, where at least two of the projections are in spaced relation from one another angularly about the longitudinal axis on the inner bore surface, and at least two of the projections are in spaced relation relative to one another longitudinally on the inner bore surface. As can be appreciated, these can be the same two projections, such that the two are spaced angularly and longitudinally relative to one another. Optionally, more than two projections can be provided with some projections spaced angularly relative to one another, and some projections spaced longitudinally relative to one another. The projections can also be positioned in any arrangement (angularly and/or longitudinally) that results in the line of sight from the input end to the output end being substantially obstructed. As used herein, the term "line of sight" is intended to mean any straight line along which a ray of light would travel. Thus, if the line of sight from the input end to the output end is substantially obstructed, the majority of light rays would be prevented from passing through the tube. It is also contemplated that the projections can be positioned in any arrangement that results in the line of sight from the input end to the output end being completely obstructed.

An exemplary projection as described herein, such as projection 130 shown in FIG. 1E, can have a base 136 and an opposed apex 137, and a predetermined height h measured from the base to the apex. The height h can be measured along a second axis 140 that is transverse to the longitudinal axis 114. The second axis can be at an angle of about 90 degrees relative to the longitudinal axis, or at an angle greater than or less than 90 degrees. As shown in FIG. 1E, the predetermined height h can be greater than a distance r from the base to the longitudinal axis measured along the second axis. Thus, if the bore 120 has a substantially circular cross section, it is contemplated that at least one projection can extend from the inner bore surface 122 into the bore at a distance greater than the radius of the bore. The height h can be a distance slightly less than the inner diameter d of the bore, such that it comes close to but does not touch an opposing portion of the inner bore surface from where it projects. Optionally, the height h can be less than the distance r from the base to the longitudinal axis.

As shown in FIGS. 1A and 2A, at least one projection (130 or 230) can be positioned in a portion of the bore proximate to the output end of the bore. For example, if the tube 112 has a lower half comprising the output end 118, and an upper half comprising the input end 116, the at least one projection can be positioned in the bore in the lower half of the tube. Optionally, the at least one projection can be positioned in the bore in a lower third of the tube. In yet another example, the at least one projection can be positioned anywhere along the length of the bore.

Exemplary projection(s) as described herein can be formed according to known methods. For example, and not meant to be limiting, the projections of the inlet liner can be formed in a glass tube by heating portions of the glass and pressing on them (on the outside of the tube), such as with a steel rod, to form a projection inside the bore of the tube.

Figure 5:
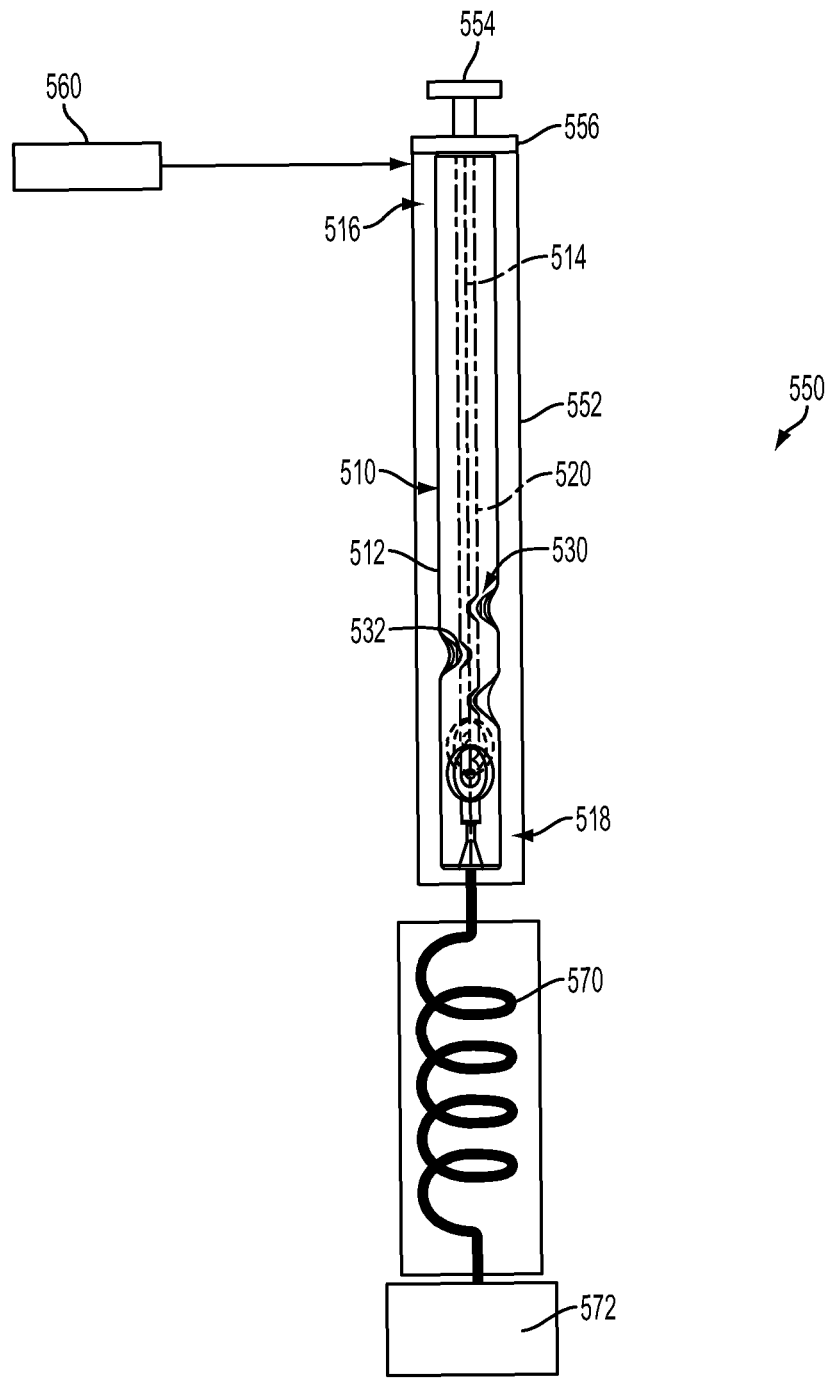
FIG. 5 is a schematic diagram of a chromatograph system, according to one aspect.

According to various aspects, a chromatograph system 550 is provided, such as shown in FIG. 5. The chromatograph system 550 can comprise a chromatograph column 570, an analyzer 572 in fluid communication with the chromatograph column, and an inlet assembly 552 connectable to the chromatograph column. The chromatograph system can also comprise an inlet liner 530, such as the exemplary inlet liners described herein, the inlet liner being positionable in the inlet assembly. Thus, the inlet liner 530 can comprise an elongate tube that extends along a longitudinal axis 514 and has an input end 516 configured to receive a sample and an oppositely disposed output end 518 in fluid communication with the chromatograph column 570. The elongate tube can define a bore 520 that extends along the longitudinal axis and has an inner bore surface. The bore can be configured to pass the sample to the chromatograph column. The inlet liner can also comprise at least one projection 530 extending from the inner bore surface into the bore. In one particular example, the inlet liner can comprise a plurality of projections that are positioned in the bore such that a line of sight from the input end 516 to the output end 518 is substantially obstructed. For example, the plurality of projections can be spaced longitudinally and/or angularly relative to one another (such as described above), in any manner that substantially obstructs the line of sight from the input end to the output end.

It is contemplated that the chromatograph system can comprise other components known in the art, such as a sample injector 554 that is configured to inject the sample through a septum 556 of the inlet assembly 552. The chromatograph system can also comprise a carrier gas source 560 that is configured to pass a carrier gas into the inlet liner to be mixed with the sample (such as is known in the art). The exemplary chromatograph system 550 can operate in split/splitless modes or in programmed temperature mode, as is known in the art. Similarly, it is contemplated that exemplary inlet liners as described herein can be used in any known chromatograph system, and is not intended to be limited to use in the exemplary chromatograph system 550 described herein.

Figure 1F:
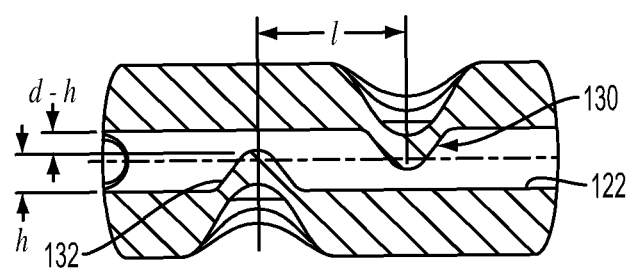
FIG. 1F is a cross-sectional view of the inlet liner of FIG. 1A on an enlarged scale as shown in circle 1F of FIG. 1D.
Figure 6:
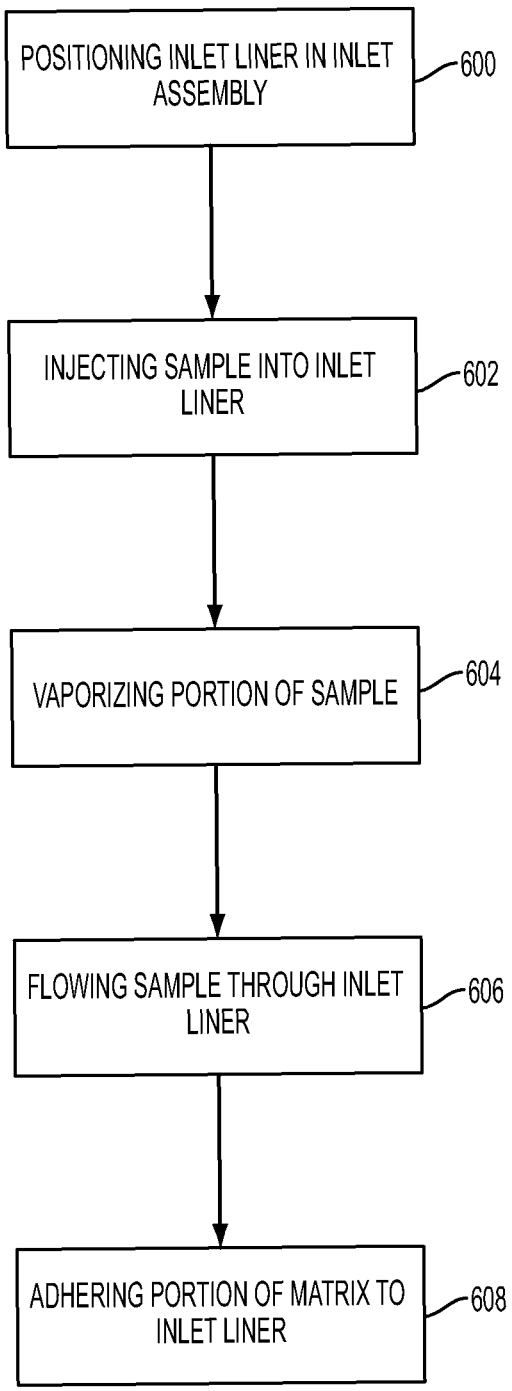
FIG. 6 is a flow chart depicting an exemplary method for analyzing a sample, according to one aspect.

According to various other aspects, methods are provided for analyzing a sample containing a matrix in a chromatograph system having an inlet assembly connected to a chromatograph column. It is contemplated that the exemplary methods described herein can be used to analyze any type of sample, such as, but not limited to, samples containing a food matrix (such as for food safety analyses), or environmental samples. The chromatograph system can be the exemplary chromatograph system(s) described herein, or any known chromatograph system. An exemplary method is shown in FIG. 6. The method(s) can comprise (at step 600) positioning an inlet liner in the inlet liner assembly, such as the exemplary inlet liner(s) described herein. For example, with reference to FIG. 1A or 2A, the inlet liner (110, 210) can comprise at least one projection (130, 230) extending from the inner bore surface into the bore. The at least one projection can have a projection surface (132, 232) that is oriented transverse to the longitudinal axis. For example, the projection surface (132, 232) can extend up from the inner bore surface at an angle, such as shown in FIGS. 1F and 2D.

The method can further comprise, at step 602, injecting the sample into the input end of the inlet liner and vaporizing at least a portion of the sample at step 604. As discussed above, the chromatograph system can be operated in split/splitless modes or programmed temperature mode, such as known in the art. For example, the chromatograph system can be run in "hot" mode where the inlet is run at high enough temperatures to flash vaporize the injected sample. Optionally, the chromatograph system can be run in "cold" mode, in which the inlet temperature is held at or below the sample's boiling point to allow transfer from the sample injector into the inlet liner. After the transfer, the sample injector can be removed and the inlet can be rapidly heated to vaporize the sample.

At step 606, the method comprises flowing the sample through the inlet liner toward the chromatograph column. At step 608, the method comprises adhering a portion of the matrix to the projection surface of at least one projection. Thus, the inlet liner can trap or contain portions of the matrix (such as the involatile material in the matrix) to minimize or prevent them from entering and thereafter fouling the column.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An inlet liner for use in an inlet assembly of a chromatograph system, said inlet liner comprising:
   an elongate tube extending along a longitudinal axis and having an input end and an oppositely disposed output end, wherein said elongate tube defines a bore extending along said longitudinal axis and having an inner bore surface; and
   a plurality of projections comprising a group of first projections and a group of second projections, wherein each projection extends from said inner bore surface into said bore,
   wherein
   each said first projection is spaced from a neighboring first projection at a first predetermined distance longitudinally on said inner bore surface,
   each said second projection is spaced from a neighboring second projection at a second predetermined distance longitudinally on said inner bore surface, and
   said first group of projections and said group of second projections are in spaced at any angle θ to one another about said longitudinal axis, wherein is from about 10 degrees to about 90 degrees.

2. The inlet liner of claim 1, wherein said plurality of said projections comprises 2 to 12 said first projections and 2 to 12 said second projections.

3. The inlet liner of claim 2, wherein said plurality of said projections comprises 3 to 7 said first projections and 3 to 7 said second projections.

4. The inlet liner of claim 1, wherein said angle θ is about 90 degrees about said longitudinal axis.

5. The inlet liner of claim 1, wherein each of said first and second projections comprises a proximal portion attached to said inner bore surface and a distal portion extending into said bore, and wherein said distal portion of said first projection is positioned adjacent said distal portion of said second projection.

6. The inlet liner of claim 5, wherein said angle θ is about 90 degrees about said longitudinal axis, said distal portions of said first and second projections being in abutting relationship.

7. The inlet liner of claim 1, wherein said first group of projections and said second group of projections are positioned in said bore such that a line of sight from said input end to said output end is substantially obstructed.

8. The inlet liner of claim 1, wherein said at least one said projection is positioned in a portion of said bore proximate to said output end.

9. The inlet liner of claim 1, wherein said at least one projection has a base and an opposed apex and a predetermined height from said base to said apex measured along a second axis transverse to said longitudinal axis, wherein said predetermined height is greater than a distance from said base to said longitudinal axis measured along said second axis.

10. The inlet liner of claim 1, wherein a portion of said bore proximate to said input end has an inner diameter of about 1 mm to about 6 mm.

11. The inlet liner of claim 1, wherein a portion of said bore proximate said input end has an inner diameter of about 2 mm.

12. A chromatograph system, comprising:
   a chromatograph column;
   an analyzer in fluid communication with said chromatograph column;
   an inlet assembly connectable to said chromatograph column; and
   an inlet liner positionable in said inlet assembly, said inlet liner comprising:
      an elongate tube extending along a longitudinal axis and having an input end configured to receive said sample and an oppositely disposed output end in fluid communication with said chromatograph column, wherein said elongate tube defines a bore extending along said longitudinal axis and having an inner bore surface, wherein said bore is configured to pass said sample to said chromatograph column, and
      a plurality of projections comprising a group of first projections and a group of second projections, wherein each projection extends from said inner bore surface into said bore,
   wherein
   each said first projection is spaced from a neighboring first projection at a first predetermined distance longitudinally on said inner bore surface,
   each said second projection is spaced from a neighboring second projection at a second predetermined distance longitudinally on said inner bore surface, and said first group of projections and said group of second projections are in spaced at any angle θ to one another about said longitudinal axis, wherein is from about 10 degrees to about 90 degrees.

13. The chromatograph system of claim 12, wherein said first group of projections and said second group of projections are positioned in said bore such that a line of sight from said input end to said output end is substantially obstructed.

14. A method for analyzing a sample with a chromatograph system having an inlet assembly connected to a chromatograph column, said method comprising:
   providing an inlet liner comprising:
      an elongate tube extending along a longitudinal axis having an input end and an opposed output end, wherein said elongate tube defines a bore extending along said longitudinal axis and having an inner bore surface; and
      a plurality of projections comprising a group of first projections and a group of second projections, wherein each projection extends from said inner bore surface into said bore and is oriented transverse to said longitudinal axis,
   wherein
   each said first projection is spaced from a neighboring first projection at a first predetermined distance longitudinally on said inner bore surface,
   each said second projection is spaced from a neighboring second projection at a second predetermined distance longitudinally on said inner bore surface, and
   said first group of projections and said group of second projections are in spaced at any angle θ to one another about said longitudinal axis, wherein is from about 10 degrees to about 90 degrees;

positioning inlet liner in said inlet assembly such that said output end is in fluid communication with said chromatograph column;

injecting said sample into said input end of said inlet liner;

vaporizing at least a portion of said sample;

flowing said sample through said inlet liner toward said chromatograph column; and adhering a portion of said matrix to said projection surface of said at least one said projection.

15. The method of claim 14, wherein said inlet liner has an input portion proximate to said input end and an output portion proximate to said output end, wherein said at least one projection is positioned in said output portion, and wherein said step of vaporizing comprises vaporizing at least a portion of said sample in said input portion of said inlet liner.

16. The method of claim 14, wherein said first group of projections and said second group of projections are positioned in said bore such that a line of sight from said input end to said output end is substantially obstructed, wherein said step of flowing comprises flowing said sample across said projection surfaces of said projections, and wherein said step of adhering comprises adhering portions of said matrix to said projection surface of at least one of said projections.

17. The method of claim 14, wherein said plurality of said projections comprises 2 to 12 said first projections and 2 to 12 said second projections.

18. The method of claim 17, wherein said plurality of said projections comprises 3 to 7 said first projections and 3 to 7 said second projections.

19. The method of claim 14, wherein said angle $\theta$ is about 90 degrees about said longitudinal axis.

\* \* \* \* \*